(12) United States Patent
Debroise et al.

(10) Patent No.: US 9,360,207 B2
(45) Date of Patent: Jun. 7, 2016

(54) ASSEMBLY AND METHOD FOR DETECTING AND MEASURING THE FOULING RATEOF FLOW HOLES IN A SECONDARY CIRCUIT OF A PRESSURIZED WATER NUCLEAR REACTOR

(75) Inventors: Mikael Debroise, Rully (FR); Yann Kernin, Granges (FR); Marc Piriou, Chalon sur Saône (FR); Bernard Sartre, Saint-Remy (FR)

(73) Assignee: AREVA NP, Courbevoie (FR)

( * ) Notice: Subject to any disclaimer, the term of this patent is extended or adjusted under 35 U.S.C. 154(b) by 897 days.

(21) Appl. No.: 13/110,695

(22) Filed: May 18, 2011

(65) Prior Publication Data

US 2012/0002775 A1 Jan. 5, 2012

(30) Foreign Application Priority Data

May 19, 2010 (FR) ...................................... 10 53860

(51) Int. Cl.
| | | |
|---|---|---|
| *G21C 17/017* | (2006.01) | |
| *F22B 37/00* | (2006.01) | |
| *G01N 17/00* | (2006.01) | |
| *G01N 27/87* | (2006.01) | |

(52) U.S. Cl.
CPC ............ *F22B 37/003* (2013.01); *G01N 17/008* (2013.01); *G01N 27/87* (2013.01)

(58) Field of Classification Search
None
See application file for complete search history.

(56) References Cited

U.S. PATENT DOCUMENTS

| | | | |
|---|---|---|---|
| 5,256,966 A | 10/1993 | Edwards | |
| 5,408,883 A * | 4/1995 | Clark et al. | ...................... 73/601 |
| 6,018,242 A * | 1/2000 | Piriou et al. | .................. 324/242 |
| 6,198,277 B1 * | 3/2001 | Porter et al. | .................. 324/220 |
| 2011/0241660 A1 * | 10/2011 | Gemma | ....................... 324/220 |

FOREIGN PATENT DOCUMENTS

| | | |
|---|---|---|
| DE | 43387526 | 5/1995 |
| FR | 2 459 490 | 1/1981 |
| FR | 2 692 044 | 12/1993 |
| FR | 2 927 723 | 8/2009 |
| FR | 2 928 024 | 8/2009 |
| GB | 2 055 473 | 3/1981 |
| WO | WO 2009103922 A2 * | 8/2009 |

* cited by examiner

*Primary Examiner* — Jack W Keith
*Assistant Examiner* — Lily C Garner
(74) *Attorney, Agent, or Firm* — Davidson, Davidson & Kappel, LLC

(57) ABSTRACT

An assembly for detecting and measuring the fouling rate by deposits containing at least one ferromagnetic material, including a probe which can be continuously moved inside a tube and which has a body carrying on its outer surface at least one magnetized source for self-orientation of the body of the probe, at least three magnetic field emitters and at least three magnetic field detectors each positioned between two contiguous emitters.

17 Claims, 6 Drawing Sheets

ASSEMBLY AND METHOD FOR DETECTING AND MEASURING THE FOULING RATE OF FLOW HOLES IN A SECONDARY CIRCUIT OF A PRESSURIZED WATER NUCLEAR REACTOR

This application claims priority to French application FR 10 53860, filed on May 19, 2010, the entire disclosure of which is incorporated by reference herein.

The present invention concerns an assembly for detecting and measuring the fouling rate of flow holes for secondary circuit water in the tube support plates of a steam generator of a pressurized water nuclear reactor.

BACKGROUND

Pressurized water nuclear reactors comprise steam generators which ensure the heating and vaporization of feed-water via the heat conveyed by the pressurized water used to cool the core of the reactor. Pressurized water reactors, on each of their primary branches, comprise a steam generator having a primary part in which the pressurized water for cooling the reactor circulates, and a secondary part receiving the feed-water which is heated and progressively vaporized and then leaves the secondary part of the steam generator in the form of steam which is sent to a turbine associated with the nuclear reactor to ensure the driving of an alternator producing electric current.

Said steam generators comprise an outer shell called a pressure shell generally of cylindrical shape and arranged with its axis positioned vertically and secured to a substantially horizontal tube sheet whose lower face or inlet face forms a wall of the plenum of the steam generator fed with pressurized water forming the primary fluid.

The steam generator also comprises a bundle of U-bend tubes, each comprising two straight branches parallel to one another whose ends are secured in holes passing through the tube sheet between the lower inlet side of the tube sheet and the upper outlet side from which the tubes of the bundle are held in position in the secondary part of the steam generator, in which part an inner wrapper, called the bundle wrapper arranged in coaxial position inside the pressure shell, delimits an annular space with this pressure shell.

The tubes of the bundle are additionally held in regular position over transverse planes perpendicular to the axis of the bundle, via tube support plates which are distributed at regular distances over the height of the bundle.

A network of openings passes through the tube support plates, this network being identical to the network of openings of the tube sheet of the steam generator.

These tube support plates which hold the tubes of the tube bundle within the bundle wrapper are provided with flow holes for secondary water along the tubes of the bundle, the holes passing through the thickness of each tube support plate and being lobe-shaped, called trefoil or quatrefoil flow holes.

During the functioning of the steam generator, the circulating feed-water in contact with the outer surface of the tubes of the bundle and inside the secondary circuit of the reactor, picks up impurities of various types and in particular of magnetite type which may be deposited in the form of sludge in different parts of the steam generator and in particular in the spaces between the tubes of the bundle and the flow holes provided in the tube support plates to allow the coolant water to circulate around the tubes of the bundle.

The deposits which accumulate between the flow holes of the support plates and the outer surface of the tubes of the bundle progressively clog these flow holes preventing circulation of coolant water and may produce some encasing of the tubes in the holes, which means that the tubes become rigidly fixed in the tube support plate preventing their movement in the axial direction common to the flow hole and the tube, and also causing their immobilization in the radial directions.

Under these conditions, the thermal yield of the steam generator is largely degraded, and in extreme cases there is a risk that the tubes may be subjected to stress above the tube support plates and may subsequently become cracked, causing a leak of primary water into the secondary circuit leading to shutdown of the nuclear reactor.

To measure the fouling rate of these deposits which accumulate between the flow holes of the tube support plates and the outer surface of the tubes, a probe is known from FR-2 927 723 also to the Applicant, this probe comprising a body of general cylindrical shape having on its outer surface at least two magnetic field detectors arranged co-axially and secured to said body, and containing at least one permanent magnet co-axial to this body whose North-South orientation coincides with the longitudinal axis of the body, said at least two detectors being connected by connection means to a system amplifying and displaying variations in the signals transmitted by these detectors when the probe is moved inside a tube of the steam generator. FR 2928024, FR 2459490 and DE 4338752 also teach probes for detecting deposits. U.S. Pat. No. 5,256,966 discloses a method and apparatus for inspecting the profile of the inner wall of a conduit by a probe body that includes eddy current sensing coils. FR 2692044 discloses a robotic sampling device for cutting a part of a tube wall for sampling where the sample can be mounted onto a separate tube for testing the physical properties of the cut wall portion and a video probe can be passed through the window to monitor conditions near the support plates and tube sheets.

Each flow hole of the tube support plates is shaped with three of four lobes or alveoli, called trefoil or quatrefoil respectively.

Therefore, each flow hole is formed of alternating alveoli and solid portions in contact with a tube.

Measurement of fouling rate using this type of probe corresponds to a mean for the flow hole as a whole i.e. the total number of alveoli.

Yet, this phenomenon of fouling in each of the flow holes is not uniform and one alveolus may be clogged to a greater extent than neighbouring alveoli. In addition, the localization of the deposits in a given alveolus is variable and they may lie preferably on the tube side or on the side of the tube support plate, or they may be uniformly distributed around the entire periphery of the cross-section of the flow hole. On account of its operating principle, the above-mentioned probe is sensitive to the distance between the measured deposit and the detector and therefore entails some measurement uncertainty related to the geometry of the deposit.

SUMMARY OF THE INVENTION

To measure the fouling rate of each alveolus independently, either a rotating probe must be used which has some disadvantages regarding its implementation since it must comprise on-board motorization and the inspection time is relatively long, or a multi-element probe but the angle coverage thereof to intercept useful data requires a high number of detection elements leading to the complex fabrication and interfacing of this type of probe.

An objective of the invention is therefore to avoid these shortcomings and to propose a device and a method having simple, easy-to-implement means which can be used to detect and accurately estimate the fouling rate of each alveolus independently of the flow holes of tube support plates in the secondary circuit of steam generators.

The invention provides an assembly for detecting and measuring the rate of fouling, by deposits containing at least one ferromagnetic material, of the flow holes of tube support plates in a secondary circuit of a steam generator, of a pressurized water nuclear reactor, said steam generator comprising a tube bundle for circulation of primary water, the vertical branches of the tubes being held in flow holes of the tube support plates, each having at least three alveoli separated by solid portions in contact with a tube, characterized in that it comprises a probe which can be continuously moved inside a tube of the bundle and comprising a body of cylindrical elongate shape carrying firstly on its outer surface at least one magnetized source for self-orientation of the body of the probe relative to the solid portions of the flow holes, and secondly at least three magnetic field emitters each intended to be automatically positioned opposite a solid portion when the probe moving in the tube arrives at each flow hole, and in that the body of the probe contains at least three magnetic field detectors each positioned between two contiguous emitters, the assembly of detectors being connected via connection means to a system for amplifying and displaying signals transmitted by said detectors when the probe moving in the tube arrives at each flow hole to be inspected in the tube support plates.

According to other characteristics of the invention:
said emitters and said detectors are arranged on one same circumference of the body of the probe,
said at least one magnetized source is arranged in front of the circumference formed by said emitters and said detectors relative to the direction of travel of the probe in the tube,
said at least one magnetized source is arranged behind the circumference formed by said emitters and said detectors relative to the direction of travel of the probe in the tube,
said at least one magnetized source comprises at least one first magnetized source and at least one second magnetized source arranged either side of the circumference formed by said emitters and said detectors,
said at least one magnetized source is formed by a permanent magnet or an electro-magnet whose North-South orientation coincides with the radial axis of the body of the probe,
there are three said emitters distributed at 120° on the circumference, or four emitters distributed at 90° on this circumference,
there are three said detectors distributed at 120° on the circumference, or four distributed at 90° on this circumference,
each emitter is formed by a permanent magnet or an electro-magnet of which one of the poles is directed radially towards the outside of the body of the probe,
said at least one magnetized source is arranged on the same generatrix of the probe body as an emitter,
each emitter is formed by an emitting coil,
each emitting coil is arranged on a substantially median generatrix of the body between two magnetized sources,
each magnetic field detector is formed by a magnetometer, and
the emitters ensure the angular self-positioning role of the magnetized sources.

A further object of the invention is to provide a method for detecting and measuring the rate of fouling, by deposits containing at least one ferromagnetic material, of the flow holes in the tube support plates of a secondary circuit of a steam generator of a pressurized water nuclear reactor, via a detecting and measuring assembly such as defined above, characterized in that:

at least one freely rotating probe is inserted into at least one tube of the tube bundle of the steam generator,
said at least one probe is moved at a determined rate inside said at least one tube, said at least one magnetized source automatically orienting the body of the probe to position each magnetic field emitter opposite a solid portion of a flow hole and each magnetic field detector opposite an alveolus of said flow hole, and
the variations in the signals transmitted by said detectors—when the said at least one probe travelling in said at least one tube arrives at each flow hole to be inspected of the tube support plates—are amplified and displayed.

According to another characteristic, in relation to the variations in the signals transmitted by said detectors, the distribution of deposits is mapped for at least one region of the tube support plates of the steam generator.

BRIEF DESCRIPTION OF THE DRAWINGS

The characteristics and advantages of the invention will become apparent in the following description given as an example and with reference to the appended drawings, in which.

DETAILED DESCRIPTION

Figure 1:
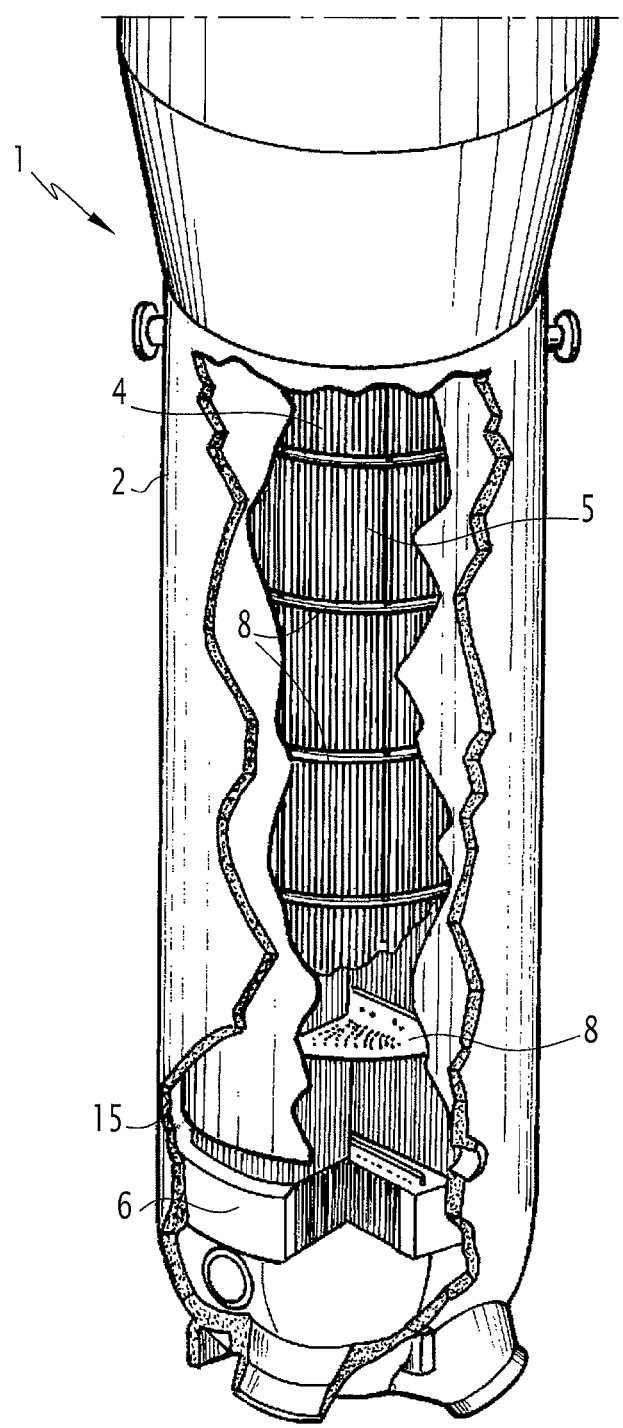
FIG. 1 is a schematic, perspective view of a steam generator of a pressurized water nuclear reactor.

FIG. 1 illustrates the lower part of a steam generator of a pressurized water nuclear reactor, generally designated under reference number 1. The steam generator 1, as is conventional, comprises a pressure shell 2 of substantially cylindrical shape inside which a bundle wrapper 4 is arranged co-axially containing a tube bundle 5 of the steam generator 1.

The tube bundle 5 is formed of a very high number of tubes 5 bent in a U-shape, each comprising two straight branches whose ends are engaged in and secured to a tube sheet 6 fixed to the lower part of the pressure shell of the steam generator 1.

The pressure shell 2 is connected to a semi-spherical bottom part delimiting a plenum in two parts.

Inside the tube bundle wrapper 4, at successive positions over the height of the bundle, tube support plates are fixed 8 intended to hold in position the branches of the tubes 5 of the bundle 4 to prevent them from vibrating when the steam generator is in operation.

Each of the tube support plates 8 is pierced with a network of openings similar to the network of openings passing through the tube sheet 6 in which the ends of the tubes 5 of the bundle 4 are secured. The straight branches of the tubes 5 of the bundle are engaged in the aligned openings of tube support plates 8 spaced apart in the longitudinal direction of the tube 5.

Figure 2:
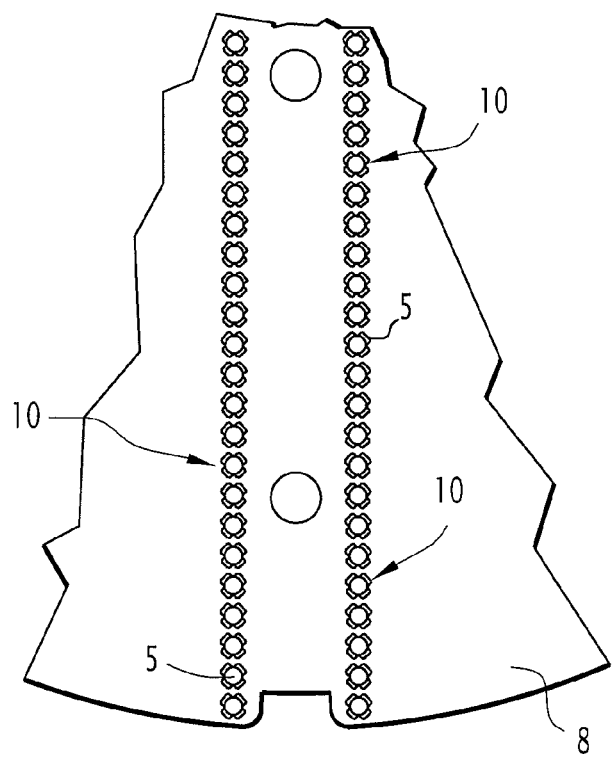
FIG. 2 is a partial, schematic overhead view of a quatrefoil tube support plate of a steam generator of a pressurized water nuclear reactor.
Figure 5:
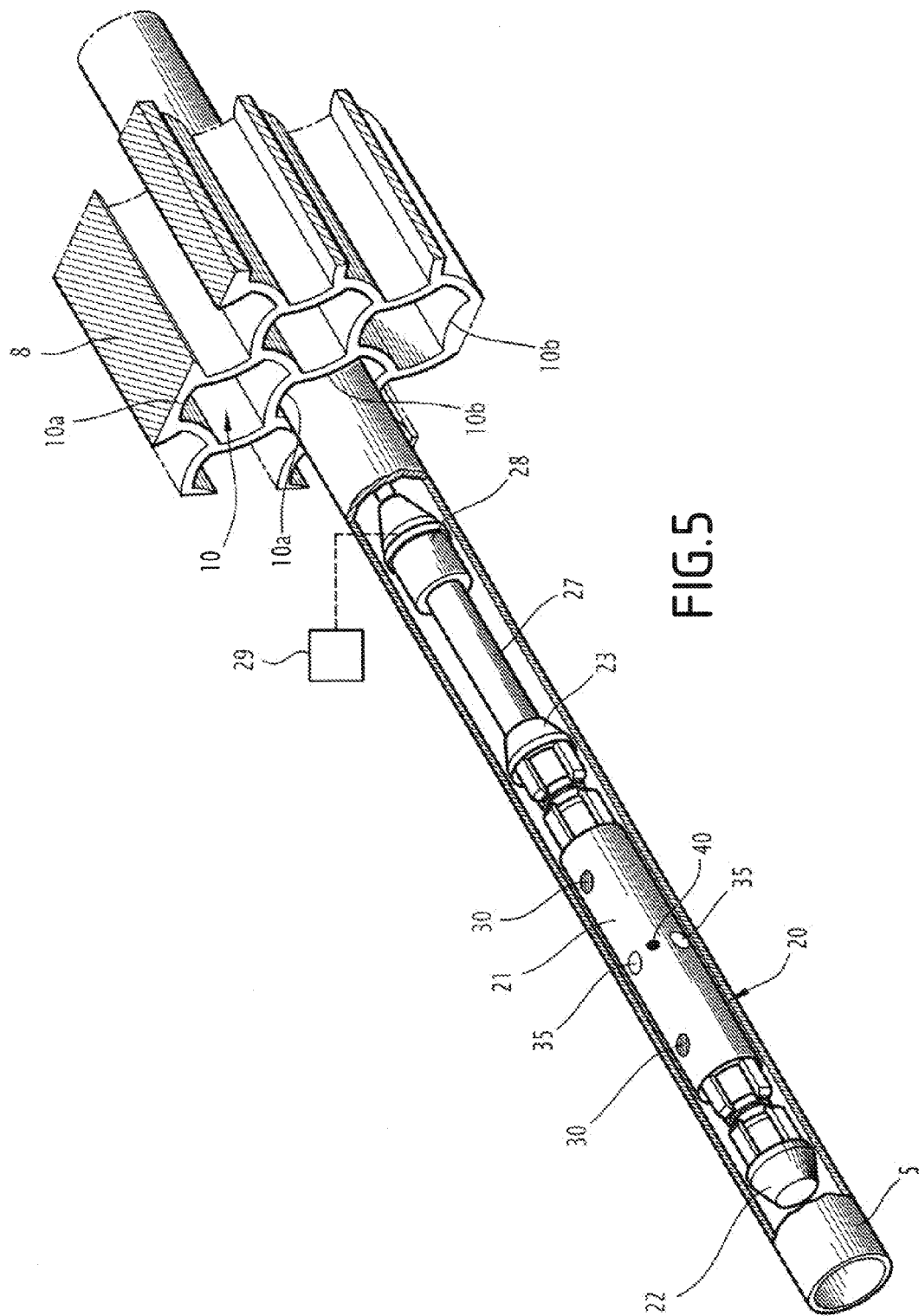
FIG. 5 is a schematic, partial cut-away view of a tube of a steam generator, showing the position of a probe in a tube with a trefoil tube support plate.

Therefore, as shown FIG. 2, holes 10 for the tubes 5 of the bundle 4 pass through each tube support plate 8, and these holes 10 in the example of embodiment shown in this figure have a shape comprising four alveoli, these holes 10 then being called quatrefoil holes. These holes may be shaped with three alveoli, called trefoil holes, as shown in FIG. 5.

These holes 10 are therefore each formed of at least three alveoli 10a separated by solid portions 10b in contact with a tube 5. These alveoli 10a allow the passing of feed-water of the steam generator circulating in the vertical direction from bottom upwards.

Figure 3:
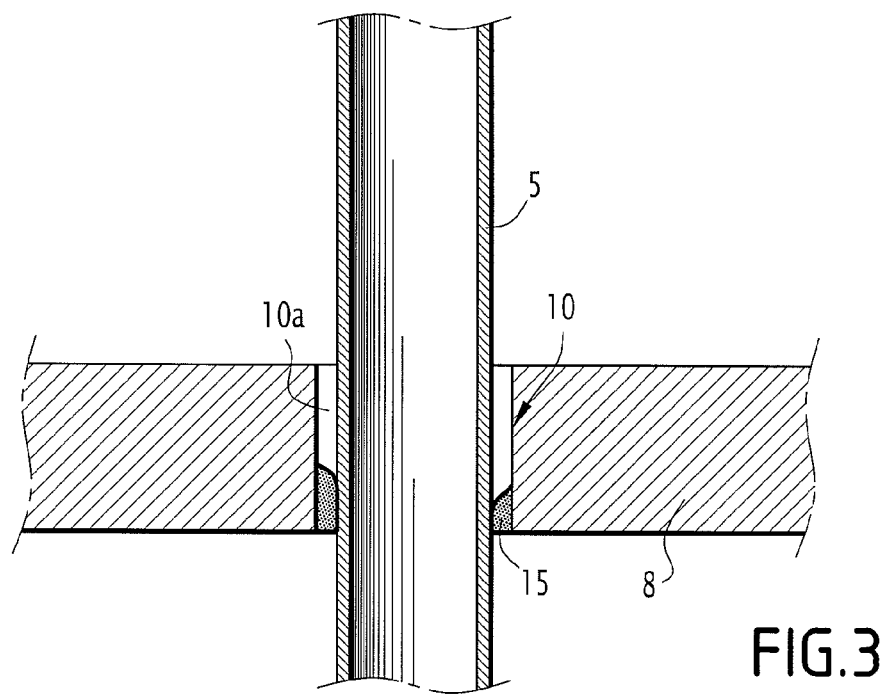
FIG. 3 is vertical section, schematic view of a passageway for a tube of a tube bundle in a tube support plate.

The water circulating in the secondary circuit and inside the secondary part of the steam generator, in contact with the outer surface of the tubes 5 of the bundle 4, picks up impurities which form deposits 15 (FIG. 3) on the tube support plates 8, in particular in the alveoli 10a between the tubes 5 and the flow holes 10 of these tube support plates 8 which must ensure the holding in position of the tubes 5 and the passing of feed-water in contact with the outer surface of the tubes 5.

These deposits contain at least one ferromagnetic material of magnetite type, and it has been ascertained that fouling of the flow holes 10 starts at the lower part, i.e. from the lower face of the tubular plate 8 and progresses upwardly by accumulation over the time the reactor is in operation.

When a reactor is shut down after a certain operating time, it is necessary to be able to detect the presence of this deposit, and also to measure the fouling rate of the holes 10 and more particularly of each of the alveoli 10a of the tube support plates 8.

Figure 4:
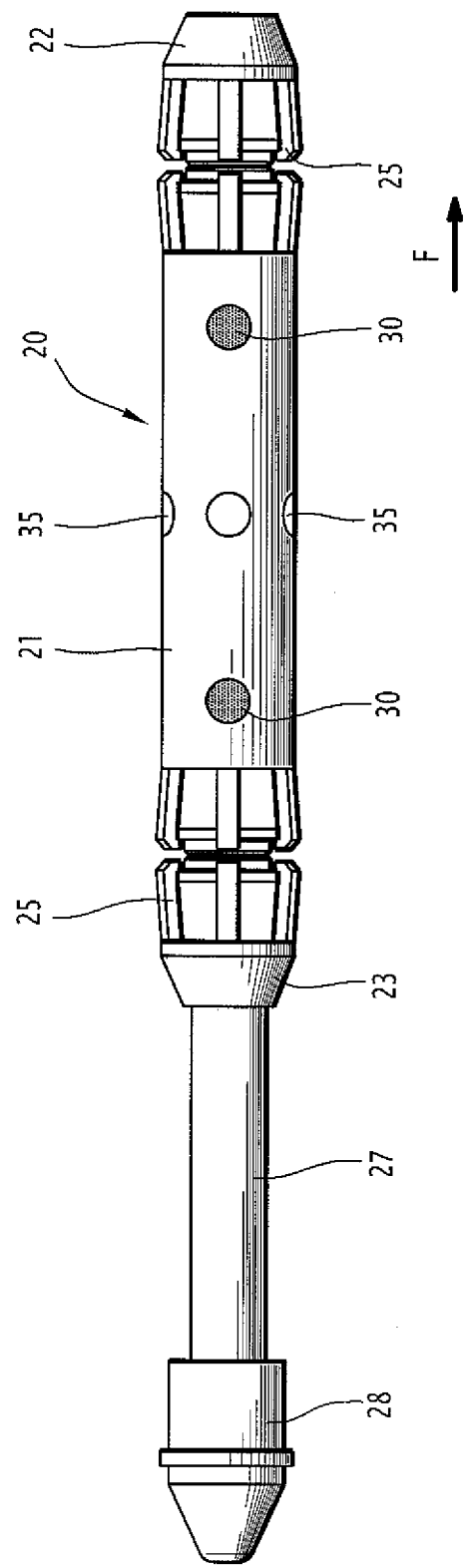
FIG. 4 is a schematic elevation view of a probe of a detecting and measuring assembly according to the invention.

For this purpose, the detecting and measuring assembly of the invention is formed of a probe illustrated FIGS. 4 and 5 given the general reference number 20.

The probe 20 comprises a body 21 of general cylindrical shape and preferably made in a material not having any magnetic characteristics. The body 21 is closed at one of its ends by a head plug 22 of conical shape and at the other of its ends by a tail plug 23.

The body 21 of the probe 20 is freely rotatable in the tube 5 in which said probe is moved and this body 21, on its periphery, comprises centring means 25 to maintain said body substantially in the longitudinal axis of the corresponding tube 5. As illustrated FIG. 4, the centring means are formed by two rings 25 mounted in the vicinity of the head plug 22 and tail plug 23 respectively. Preferably, these rings 25 are elastic to ensure self-centring of the body 21 in the tube 5. Other self-centring systems can be used, such as a mechanical system of spring type for example.

The body 21 of the probe 20 carries firstly on its outer face at least one magnetized source 30 for self-orientation of this body 21 relative to the solid portions 10b of the flow holes 10, and secondly at least three magnetic field emitters 35 each intended to be automatically positioned opposite a solid portion 10b when the probe 20 moving in the tube 5 arrives at each flow hole 10.

Figure 6:
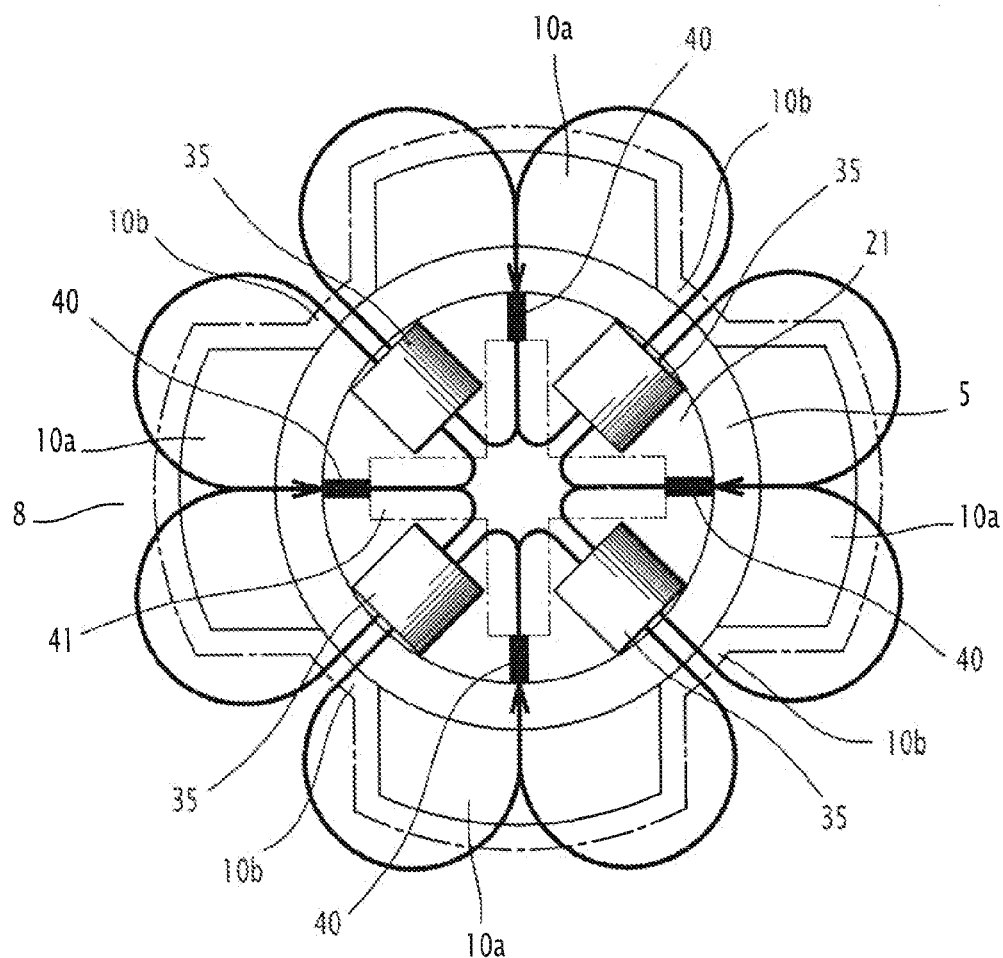
FIG. 6 is schematic cross-sectional view of the probe showing the pathway of the field lines produced by the magnetic field emitters in one of the possible configurations.

As illustrated FIG. 6, the body 21 of the probe 20 contains at least three magnetic field detectors 40 each placed between two contiguous emitters 35.

Figure 7:
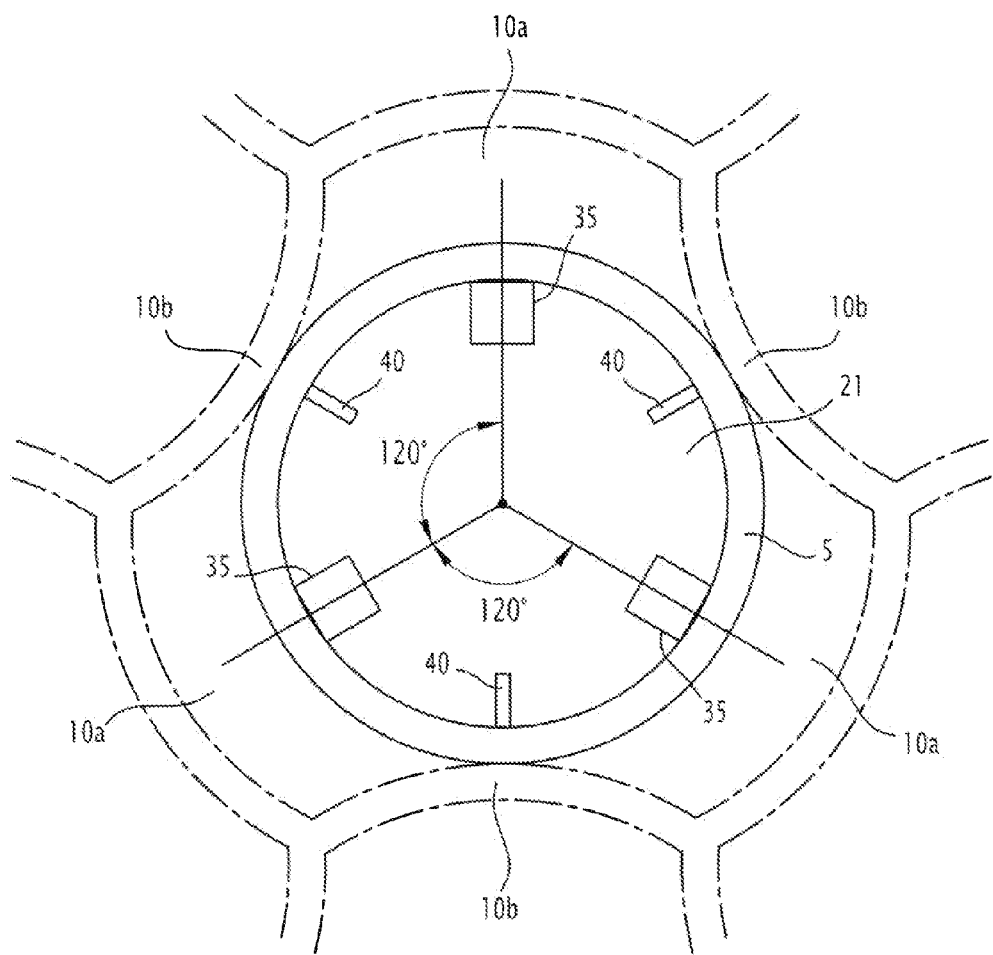
FIG. 7 is schematic cross-sectional view of the probe shown in FIG. 5.

The emitters 35 and the detectors 40 are arranged on one same circumference of the body 21 of the probe 20. If the flow hole 10 is quatrefoil i.e. comprising four alveoli 10a separated by four solid portions 10b, the emitters 35 and the detectors 40 total four in number distributed at 90° over the circumference, and if the flow hole 10 is trefoil i.e. comprising three alveoli 10a separated by three solid portions 10b, the emitters 35 and the detectors 40 are three in number distributed at 120° over the circumference, as shown schematically in FIG. 7.

In the embodiment illustrated FIG. 4, said at least one magnetized source 30 comprises at least one first magnetized source 30 and at least one second magnetized source 30 arranged on either side of the circumference formed by the emitters 35 and the detectors 40.

According to a first variant, at least one magnetized source 30 is arranged in front of the circumference formed by the emitters 35 and detectors 40 relative to the direction of travel of the probe 20 in the tube 5, indicated by the arrow F in FIG. 4.

According to a second variant, said at least one magnetized source 30 is arranged behind the circumference formed by the emitters 35 and the detectors 40 relative to the direction of travel F of the probe 20 in the tube 5.

Several magnetized sources 30 can be placed on one same circumference of the body 21, either side of the circumference defined by the emitters 35 and the detectors 40, or in front of or behind this circumference.

Each magnetized source 30 is formed by a permanent magnet or electro-magnet whose North-South orientation coincides with the radial axis of the body 21 of the probe 20.

Each emitter 35 is formed by a permanent magnet or electro-magnet whose North pole is directed towards the outside of the body 21 of the probe 20 and in this case the, or each, magnetized source 30 is arranged on the same generatrix of the body as an emitter 35.

According to one variant, each emitter 35 is formed by an emitting coil and in this case each emitting coil is arranged on a median generatrix between two magnetized sources 30.

Finally, each magnetic field detector 40 is formed by a magnetometer.

As shown FIG. 6, in the body 21 of the probe 20 a magnetic circuit 41 allows maximisation of the magnetic flow at the detectors 40.

These detectors 40 are connected by conductor wires, extending along the body 21 as far as the tail plug 23. This tail plug 23 comprises an extension 27 located in the axis of the body 21 and provided at its free end with a connector 28 connected to the conductor wires of the detectors 40. The connector 28 is preferably a rotating connector allowing the free rotation of the body 21 in the corresponding tube 5.

A magnetic circuit, can be associated with each of the magnetized sources 30 to confine the magnetic field outside the measuring area so as not to perturb measurement.

The magnetized sources 30 can also be arranged opposite the measuring magnets 35 in order to limit spreading of the field lines along the axis of the tube 5 and thereby improve the axial resolution of the measuring assembly. In this case, the number and the angle arrangement of the guiding magnetized sources 30 and the measuring magnets 35 are identical.

According to another embodiment, the emitters 35 may ensure the angular self-positioning role of the magnetized sources 30. In this case the magnetized sources 30 are not necessary.

The detection and the measurement of the fouling rate by deposits 15 in each of the alveoli 10a of the flow holes 10 of a tube support plate 8 in the secondary circuit are performed as follows.

Via an inspection port of one of the plenums of the steam generator (which can be seen FIG. 1) a probe 20 is inserted inside a tube 5 of the bundle 4. This probe 20 is connected to a system 29 (FIG. 5) amplifying and displaying variations in the signals transmitted by the detectors 40.

Using suitable means of known type, for example a boom or a probe puller/pusher positioned outside the plenum of the steam generator, the probe 20 is moved inside the tube 5 which it is desired to inspect for fouling of the flow holes of the tube support plates 8 through which the tube 5 is passed.

When approaching the tube support plate 8, the magnetized source(s) 30 positioned in front of the magnetic field emitters 35 are attracted by one of the solid portions 10b of the flow hole 10. The probe 20 therefore aligns itself in a given angular position. In this position, each magnetic field emitter 35 also positions itself in front of a solid portion 10b of the flow hole 10 and each magnetic field detector 40 positions itself in front of an alveolus 10a.

For emitters 35 consisting of permanent magnets, the North pole of each of these magnets is oriented towards the wall of the tube 5, and the South pole towards the inside of the body 21 of the probe 20, or conversely. The magnets therefore oppose each other two by two.

These magnets 35 also take part in the orientation of the probe 20 so that each of these magnets 35 is positioned opposite a solid portion 10b.

According to the principle of the path of least magnetic reluctance in a magnetic circuit, the field lines shown in FIG. 6 are guided by the tube support plate 8. These field lines are captured by the solid portions 10b and follow the contour of the alveolus 10a. In the median plane of each alveolus 10a, the field lines derived from two neighbouring magnets 35 oppose one another. This opposition within the tube support plate 8 causes a leak flux or airgap of the magnetic circuit in the central region of each alveolus 10a, the field lines looping back towards the South pole. By placing the magnetic field detector 40 directly above this region, information is retrieved on the fouling rate of each alveolus 10a. The magnetic circuit 41 allows maximization of magnetic flux at the detectors 40.

The probe 20 of the detecting and measuring assembly according to the invention allows precise, complete measurement through differentiated treatment of the deposits in each alveolus 10a of the flow hole 10 to be inspected. The preferable use of measurement magnets whose North-South orientation is arranged radially relative to the axis of the tube allows measurement based on the principle of the closing of a magnetic circuit, and not on the deflection of field lines as in detection devices used up until now. The accuracy of measurement is thereby improved since the result is not a function of the localization of the deposits in each alveolus.

According to one variant, the body 21 of the probe 20 may have freedom of rotation in the tube that is limited to around an equilibrium position, for example a travel distance of one third of a turn i.e. more or less 60°. If there are no tube support plates 8 in the vicinity of the probe 20, the body 21 of this probe is held in its equilibrium position by suitable members such as return springs. The stiffness of these springs is such that, on approaching the tube support plate 8, the torque set up by the magnetizing force exceeds the return torque set up by the springs. In this variant, the conductor wires may be connected to the measurement apparatus by means of coaxial cables which avoids the use of a rotating connector.

If emitting coils are used instead of permanent magnets, the distance between the magnetized sources 30 for self-orientation, positioned either side of the circumference defined by the emitters 35 and the receivers 40, must be shorter than the height of the tube support plate 8 in order to maintain the angular alignment of the body 21 of the probe 20 over the entire height of the tube support plate 8.

To pass through the bent parts of the tubes of steam generators, the magnetized sources 30 and the measurement assembly formed of the emitters 35 and detectors 40 can be separated into several parts mechanically connected together via a flexible link but which is joined in rotation.

The assembly of the invention, using low-cost and simple means, therefore allows rapid performing of the detection and measurement of the fouling rate of each of the alveoli of each flow hole in the tube support plates of a secondary circuit of a steam generator, to determine whether or not cleaning of these flow holes of these plates is necessary.

In general, the invention applies to the detection and measurement of the rate of fouling by deposits containing at least one ferromagnetic material in the flow holes of any steam generator or heat exchanger comprising a tube bundle held in position by tube support plates in which water flow alveoli are arranged.

What is claimed is:

1. An assembly for detecting and measuring a rate of fouling, by deposits containing at least one ferromagnetic material, of flow holes in tube support plates of a secondary circuit of a steam generator of a pressurized water nuclear reactor, the generator comprising a bundle of primary water circulation tubes, vertical branches of the tubes being held in the flow holes of the tube support plates, each flow hole having at least three alveoli separated by solid portions in contact with one of the tubes of the bundle, the assembly comprising:
   a probe which can be moved inside and along one of the tubes of the bundle of primary water circulation tubes, the probe comprising a body of cylindrical elongate shape with a central longitudinal axis, the body carrying on its outer surface at least three magnetic field emitters for emitting a magnetic field, the body of the probe containing at least three magnetic field detectors for detecting the magnetic field, each magnetic field detector being positioned between two angularly consecutive magnetic field emitters,
   the body carrying on its outer surface at least one magnetized source for angular self-orientation of the body of the probe relative to the solid portions of the flow holes, arranged such that the at least three magnetic field emitters are each automatically angularly positioned opposite one of the solid portions and the at least three magnetic field detectors are each automatically angularly positioned opposite one of the alveoli when the probe inside the tube is moved to each flow hole,
   an assembly of the magnetic field detectors being connected by a connector to a system for amplifying and displaying signals transmitted by the magnetic field detectors when the probe moving in the tube arrives at each flow hole to be inspected in the tube support plates,
   the at least one magnetized source being a permanent magnet or an electro-magnet, the magnetized source having a North-South magnetic axis extending radially from the central longitudinal axis of the body of the probe.

2. The assembly according to claim 1 wherein the magnetic field emitters and the magnetic field detectors are arranged on a same plane perpendicular to the central axis.

3. The assembly according to claim 1 wherein the at least one magnetized source is in front of a circumference formed by the magnetic field emitters and the magnetic field detectors relative to a direction of travel of the probe in the tube.

4. The assembly according to claim 1 wherein the at least one magnetized source is behind the circumference formed by the emitters and the detectors relative to a direction of travel of the probe in the tube.

5. The assembly according to claim 1 wherein the at least one magnetized source comprises at least one first magnetized source and at least one second magnetized source arranged on either side of the circumference formed by the emitters and the detectors.

6. The assembly according to claim 2 wherein the body has three magnetic field emitters distributed at 120° from one another around the central axis, the body having three magnetic field detectors distributed at 120° from one another around the central axis and angularly shifted from 60° around the central axis with regard to the magnetic field emitters.

7. The assembly according to claim 2 wherein the body has four emitters and detectors distributed at 90° over the circumference.

8. The assembly according to claim 1 wherein each magnetic field emitter is a permanent magnet or an electro-magnet having one pole directed radially towards an outside of the body of the probe.

9. The assembly according to claim 1 wherein the at least one magnetized source and at least one of the magnetic field emitters are arranged on a line substantially parallel to the central axis of the body.

10. The assembly according to claim 1 wherein each magnetic field emitter is an emitting coil.

11. The assembly according to claim 10 wherein each emitting coil is arranged on a line substantially parallel to the central axis of the body and substantially median between the magnetized source and a second magnetized source.

12. The assembly according to claim 1 wherein each magnetic field detector is a magnetometer.

13. A method for detecting and measuring a rate of fouling, by deposits containing at least one ferromagnetic material, of flow holes in tube support plates of a secondary circuit of a steam generator of a pressurized water nuclear reactor, using a detecting and measuring assembly according to claim 1, the method comprising the following steps:

inserting at least one freely rotating probe into at least one tube of a bundle of tubes of the steam generator, moving the at least one probe at a determined rate inside the at least one tube, automatically orienting a body of the probe by at least one magnetized source to position each magnetic field emitter opposite a solid portion of the flow hole and each magnetic field detector opposite an alveolus of the flow hole, and transmitting the variations in the signals transmitted by the detectors when the at least one probe moving in the at least one tube arrives at each flow hole to be inspected in the tube support plates are amplified and visualized.

14. The method according to claim 13 wherein the variations in the signals transmitted by the detectors includes mapping the distribution of the deposits in each alveolus for at least one flow hole of the at least one tube support plate of the steam generator.

15. The assembly according to claim 1 wherein the body of the probe is freely rotatable in the tube.

16. The assembly according to claim 1 wherein the at least one magnetized source is arranged on the outer surface of the body such that the at least one magnetized source is magnetically attracted by one of the solid portions of the flow hole when the probe inside the tube is moved to each flow hole and the probe aligns itself in a given angular position with respect to the flow hole.

17. The assembly according to claim 1 wherein the at least three magnetic field emitters are angularly spaced from one another around the body of the probe.

* * * * *